(12) United States Patent
Pierpaoli et al.

(10) Patent No.: US 6,299,878 B1
(45) Date of Patent: *Oct. 9, 2001

(54) TRANSFERRIN GLYCANS COMPOSITION FOR THE INDUCTION OF IMMUNE TOLERANCE

(75) Inventors: Walter Pierpaoli, Belinzona; Gonzague S. Kistler, Uitikon Waldegg, both of (CH)

(73) Assignee: Cellena AG, Ebmatingen (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/983,227
(22) PCT Filed: Jul. 18, 1996
(86) PCT No.: PCT/EP96/03159
   § 371 Date: Apr. 6, 1998
   § 102(e) Date: Apr. 6, 1998
(87) PCT Pub. No.: WO97/03680
   PCT Pub. Date: Feb. 6, 1997

(30) Foreign Application Priority Data

Jul. 20, 1995 (EP) .................................................. 95401729

(51) Int. Cl.[7] .......................... A61K 31/56; A61K 31/70; A61K 35/12; C07H 1/00
(52) U.S. Cl. ..................... 424/184.1; 424/93.7; 424/520; 435/325; 514/885; 514/54; 536/1.11
(58) Field of Search ................................ 424/184.1, 520, 424/93.7; 514/54, 885, 8; 435/325; 530/395; 536/1.11

(56) References Cited

FOREIGN PATENT DOCUMENTS

0426924A1   5/1991   (EP) .

OTHER PUBLICATIONS

Spik, Geneviève et al. *Biochimie,* vol. 70, pp. 1459–1469, (1988).
de Jong, G. et al. *Clinica Chimica ACTA.,* vol. 190, pp. 1–46, (1990).
Campion, Bruno et al. *Eur. J. Biochem.,* vol. 184, pp. 405–413, (1989).
Patel, Thankor et al. *Biochemistry,* vol. 32, pp. 679–693, (1993).
Elder, John H. et al. *Proc. Natl. Acad. Sci. USA,* vol. 79, pp. 4540–4544, (Aug. 1982).

(List continued on next page.)

*Primary Examiner*—Chrstina Y. Chan
*Assistant Examiner*—F. Pierre VanderVegt
(74) *Attorney, Agent, or Firm*—Birch, Stewart, Kolasch & Birch, LLP (57) ABSTRACT

The invention pertains to a process for the production of a pharmaceutical composition effective for controlling in a recipient mammalian host, particularly man, immune reactions of the type that are involved in graft of foreign tissue or cells, particularly transplantation of foreign tissues, organs or cells, particularly of allogeneic or even xenogeneic origin, or in immunodeficiency-linked diseases, which pharmaceutical composition is characterized by an active principle consisting of pooled transferrin-derived glycans obtained from a number of donors sufficient to allow the pool to contain sufficient phenotypic information required to ensure an induction of tolerance against antigens in an immuno-depressed host grafted with said antigens, after that host had been administered an amount of such pooled transferrin glycans effective to induce said tolerance.

8 Claims, 1 Drawing Sheet

OTHER PUBLICATIONS

MacGillivray, Ross T. et al. *Proc. Natl. Acad. Sci. USA,* vol. 79, pp. 2504–2508, (1982).

Bates, George Winston et al. *The Journal of Biological Chemistry,* vol. 248, No. 9, pp. 3228–3232, (May 10, 1973).

Pierpaoli, Walter et al. *Transplantation,* vol. 26, pp. 456–458, (1978).

Yang, Funmei et al. *Proc. Natl. Acad. Sci. USA,* vol. 81, pp. 2752–2756, (May 1984).

Takasaki, Seiichi et al. *Methods of Enzymology,* vol. 83, pp. 263–268, (1982).

Pierpaoli, Walter. *Nat. Immun.,* vol. 11, pp. 356–365, (1992).

Pierpaoli, Wlater et al. *Cellular Immunol.,* vol. 52, pp. 62–72, (1980).

Pierpaoli, Walter et al. *Cellular Immunol.,* vol. 57, pp. 219–228, (1981).

Burnette, W. Neal. *Anal. Biochem.,* vol. 112, pp. 195–203, (1981).

Uzan, George et al. *Biochem. and Biophys. Res. Commun.,* vol. 119, pp. 273–281, (Feb. 29, 1984).

Williams, John. *Trends Biochem Sci,* vol. 7, pp. 394–397, (Nov., 1982).

Leger, Didier et al. *Biochem. J.,* vol. 257, pp. 231–238, (1989).

Trowbridge, Ian S. et al. *Proc. Natl. Acad. Sci. USA,* vol. 79, pp. 1175–1179, (1982).

FIG. 1

TRANSFERRIN GLYCANS COMPOSITION FOR THE INDUCTION OF IMMUNE TOLERANCE

This application is a national stage application under 35 U.S.C. §371 of PCT/EP98/03159. The contents of which are hereby incorporated by reference.

FIELD OF INVENTION

The invention relates to the production of compositions, particularly pharmaceutical compositions, containing one or several active principles capable of controlling the immune reactions of a host against allogeneic or xenogeneic cells, tissues or organs or of immuno-competent cells against an immuno-incompetent or immuno-suppressed host, particularly those immune reactions which are involved in the so-called host versus-graft reaction (HvGR) and so-called graft versus-host reaction (GvHR) or graft versus-host disease (GvHD), as well as immune reactions which are brought into play in bone marrow transplantation (BMT), i.e. when the host is transplanted with allogeneic or xenogeneic incompatible bone marrow.

DESCRIPTION OF THE RELATED ART

Series of studies have been initiated in 1978 by one of the inventors relative to the bone-marrow-engraftment-promoting activity of bone-marrow-derived factors (Pierpaoli W. et al, Transplantation 1978; 26: 456–458) and (Pierpaoli W. et al, J. Clin. and Lab. Immunol. 1985; 16:115–124). The initial observation was that the supernatant of a solution in which the bone marrow cells had been suspended (bone marrow supernatant: BM-SN) provided an engraftment-enhancing activity (Pierpaoli W. et al, Cell Immunol 1980; 52:62–72). This indicated the presence of factors able to modify the capacity of the bone marrow to be engrafted in an irradiated host for induction of permanent allogeneic or xenogeneic chimerism.

An extensive series of experiments further demonstrated that high-molecular-weight fractions obtained by ultrafiltration through porous membranes of the native BM-SN derived from rabbit marrow contained marrow-regulating factors (MRF) capable of exerting the same effect, i.e., of inducing hemopoietic chimerism across the H-2 barrier in the murine model (Pierpaoli W. et al, Cell Immunol 1981; 57:219–228). However, the results obtained were not easily reproduced, at least quantitatively; there was considerable variability in the results and the incidence of secondary disease was high. Moreover, induction of chimerism was not achieved in all of the murine H-2 combinations tested (Pierpaoli W. et al, J Lab Clin Immunol 1985; 16:115–124).

European Patent application n° EP89403103.8/0426924 Pierpaoli W. et al, Cell Immunol 1981;57:219–228 and Pierpaoli W. et al, J Lab Clin Immunol 1985;16:115–124) reported that a specific component from rabbit bone-marrow-derived fractions, namely transferrin, could be responsible for the facilitation of allogeneic and xenogeneic bone marrow engraftment that had been achieved earlier with rabbit and bovine, marrow-derived fractions. Treating lethally irradiated C57BL/6 mice transplanted with bone marrow from BALB/c donors with iron-saturated human transferrin or conalbumin, resulted in remarkably stable engraftment, avoidance of GvHD and enduring chimerism in the majority of test animals (Pierpaoli W. et al, Cell Immunol 1991;134:225–234).

Transferrins as such have been abundantly studied. They consist of two-sited, single-chain proteins capable of binding metals. They are widely distributed in physiological fluids and cells of vertebrates.

Each of the transferrin molecules consists of a single polypeptide chain, of molecular weight in the range 76,000–81,000, which contains two similar but not identical iron binding sites. Human serum transferrin contains about 5% carbohydrate, linked to the protein in two identical and nearly symmetrical branched heterosaccharide chains. It has a molecular weight of about 80,000. 1 mg of the iron-saturated protein contains about 1.4 $\mu$g iron.

The complete amino acid sequence of human plasma transferrin has recently been established by at least three groups using CNBr cleavage (CNBr) and by complementary DNA (cDNA) methods (MacGillivray, R. T. A., et al. "The complete amino acid sequence of human serum transferrin". Proc. Natl. Acad. Sci. USA 79: 2504–2508, 1982 and Uzan, G. et al. "Molecular cloning and sequence analysis of cDNA for human transferrin. Biochem. Biophys. res. Commun. 119: 273–281, 1984 and Yang, F. et al. "Human transferrin: cDNA characterization and chromosomal localization". Proc. Natl. Acad. Sci. USA 81: 2752–2756, 1984). It is composed of 678 amino acid residues, which together with the two-N-linked oligosaccharide chains exhibit a calculated molecular weight of 79,570 (of which 6% is contributed by the glucosidic moiety: MacGillivray, R. T. A. et al. and Uzan G. et al., "Molecular cloning and sequence analysis of cDNA for human transferrin". Biochem. Biophys. Res. Commun. 119:273–281, 1984). Wiliams J. ("The evolution of transferrin", Trends Biochem. Sci, 7: 394–397, 1982) has suggested the importance of sulfhydryl groups in stabilizing the iron-binding site and has traced their evolutionary development to the 17 disulfides found in human transferrin.

For a general review of the status of general knowledge about transferrins see the general publication titled "The Physiology of Transferrin and Transferrin Receptors" by Helmut A. Huebbers and Clement A. Finch in Physiological Reviews, vol. 67, No. 2, April 1987. That publication discloses also procedures for obtaining transferrin. Particularly transferrin of human origin in a biologically pure state has been disclosed in that publication. Preferred purification procedures are based on physicochemical separation steps followed by selective fixation on matrix-bound antibody or matrix-bound receptor.

Purified iron-saturated transferrin in a substantially biologically pure state, is substantially free of serum albumin proteins.

While the capability referred to above of iron-saturated human transferrin to protect lethally irradiated C5713L/6 mice recipients transplanted with bone marrow from BALB/c mice donors has been demonstrated, the engraftment-promoting activity of human transferrin in other H2-incompatible murine combinations was not as successful in all instances.

Human transferrin induced no immune tolerance in C57BL/6 mice grafted with marrow from C3H/He donors. Further work let the inventor to then consider that the promoting effects of transferrin rather varied according to the histogenetic H-2-type combination used, the promoting effect being maximal in C57BL/6 mice (H-$2^b$) grafted with BALB/c (H-$2^d$) marrow and absent in C57BL/6 mice grafted with C3H/HE (H-$2^k$) marrow (Pierpaoli W. Nat. Immun. 1992; 11:356–365).

Thus it appears that the capability of plasma-derived transferrins (Tf) to profoundly affect engraftment of allogeneic or xenogeneic bone marrow in lethally irradiated mice and to produce a lasting chimerism, depends on a matching at least to some degree of the donor's transferrins and the cell and tissue antigens in the immunosuppressed and transplanted host. Indeed an induction of a durable state of immunological unresponsiveness or "tolerance" and, accordingly, a facilitation of engraftment of donor xenogeneic or allogeneic antigens, e.g., bone marrow, in irradiated or chemically immunosuppressed recipients treated with transferrin of a same donor is obtained, when said recipients are administered with the donor's transferrins and antigens, simultaneously or sequentially. A properly timed presentation of both transferrin and antigens, e.g., human transferrin and human leukocytes in immunosuppressed mice during initial recovery of their immune tissues and cells, results later in their inability to "recognize" human donor lymphocytes and to mount an immediate- or a delayed-type immune response against the antigens of the corresponding human donor. This "tolerant" state of the recipient mice has been confirmed by the absence of cytotoxic antibodies in the "tolerant" mouse sera against the human donor lymphocytes, by the inability of "tolerant" mice to mount a cell-mediated immune reaction in vivo against human donor leukocytes, and finally by an in vitro lack of reactivity of splenocytes of the "tolerant" mouse towards irradiated human donor lymphocytes. In summary, a donor's blood plasma-derived transferrin have the remarkable capacity of inducing a state of durable unresponsiveness in an immunosuppressed recipient host administered with antigens of the same donor in the course of regeneration of stem cells and immunocompetent cells in its bone. marrow and lymphatic organs.

It would thus seem that transferrin is a major element of the self-recognition and immune mechanisms and that it participates to the development and maintenance of self-tolerance during ontogeny and adulthood. That could possibly account at least in part for the genetic polymorphism and heterogeneity of human serum transferrins possibly mimicking the "immune personality" of a human individual: see the article titled "The Biology of transferrin" of de Jong G., Dijk J. P. and Van Ejk, H. C. Clinica Chimica ACTA, 1990, 1–46, Vol. 190.

The latter Clinica Chimica Acta publication should also be used as a reference for the definition of transferrins as used herein. This expression is to be interpreted broadly. Transferrins are deemed to consist of all molecules which, as indeed provided by that article, are included in that class of compounds designated as a whole as transferrin. They include the so-called apo-transferrins, saturated transferrin, ferro-transferrins, etc.

While the above-mentioned method appears suitable to produce a safe, specific and rapid condition in a recipient host for rapid engraftment of histoincompatible cells or tissues of a donor host and even is amenable to be adapted to different species, and also to man, in a large variety of pathologies, its use will not be all too easy under many practical circumstances, particularly where such method would always necessarily involve an identity between the donor of the transferrins and the donor of the antigens to be transplanted in the recipient host.

The finding that as efficient an induction of immune tolerance in a recipient host with respect to antigens, e.g., bone marrow or organs of allogeneic or xenogeneic nature, can also be achieved upon using mixtures of transferrins obtained from a limited number of donors of the same species as that of the antigens to be transplanted (e.g., humans when the particular donor is a human, piglets when the donor is a piglet, etc.) was thus all the more remarkable. For instance an induction of immune tolerance against antigens of a human donor can be achieved in mice by a treatment thereof with human transferrins obtained from plasma mixtures resulting from the pooling of plasmas obtained from a fairly limited number of individuals. In other words it appeared that transferrins obtained from pooled plasmas—as they are used in the industry concerned with the extraction of determined blood factors from such pooled plasmas—contained enough of the phenotypic information required to ensure in mice, a specific tolerance against the antigens of most, let alone all human donors.

Hence mixtures or "pools" of transferrins (hereafter referred to as "pooled transferrin" or p-Tf) can be obtained from a limited number of donors, yet sufficient to allow said mixtures or pools to contain enough of the phenotypic information required to ensure an induction of tolerance in a given immuno-depressed recipient host grafted with antigens of a given donor host, after that recipient host had been administered an amount of such pooled transferrins.

It thus appears that the cumulated phenotypic information collected from the individuals who provided the pooled transferrins is sufficient to induce a specific immune tolerance in different recipient hosts of the same species, as if the pooled transferrins had also contained the transferrins of the individual donor of the antigens to be grafted, no matter whether that individual was among the group of individuals whose plasmas—or transferrins—were pooled, or not.

Advantageously, pooled transferrins are obtained from human plasma pools produced in the industry of blood products. Such plasma pools often originate from several hundreds to several thousands of donors. Advantageously, these transferrins result from the purification product obtained from blood of at least 1000 donors. Thus transferrin pools are readily accessible. And indeed nowadays pooled transferrins consist of hemoderivatives deemed as having no therapeutical or clinical uses. They are merely discarded.

Though no relationship has so far really been established between the genetic diversity of transferrin and the major histocompatibility complex (MHC) system in man, the serological detection and confirmation of the presence of a sufficient number of the dominant and relevant HLA can nonetheless be relied upon to verify whether plasma pools from which the corresponding pooled transferrins are to be obtained originated from a sufficient number of donors. For instance a preferred starting plasma pool should prove to contain at least 4 serologically determinable antigens of each of the so-called HLA-A, HLA-B, HLA-C, HLA-D and HLA-DR series. Reference is for instance made to FIG. 3.1, page 70 of the book titled "Medical Immunology" edited in 1979 by James Irvine, Teviot Scientific Publications, Ediburgh, Great Britain.

It has now been discovered that the immune tolerance inducing properties of transferrin are in fact concentrated in their glycan moieties.

Thus the present invention concerns more particularly a biological composition whose active principle consists of one or several transferrin-derived glycans, substantially free of transferrin polypeptide moieties, said active principle comprising enough of the phenotypic information required to ensure an induction of tolerance in a given immuno-depressed recipient host administered with said biological composition and grafted with antigens of a given donor host.

Preferred transferrin glycans are those which originate or are obtainable from the same mammalian species as the donor's.

The expression "transferrin glycans" as used throughout this patent disclosure further extends to all glycans which display a substantially same profile as those directly obtained from transferrin, as evidenced by any of the analytical methods referred to in "Tools for Glycobiology" edited in 1994 by the Company known as Oxford GlycoSystems, available from the Company itself in the U.S.A., i.e., Oxford GlycoSystems, Inc., Cross Island Plaza, 133-33 Brookville Boulevard, Rosedale, N.Y. 11422, U.S.A., or from the European branch, i.e., Oxford Glyco-Systems Ltd., Hitching Court, Blacklands Way, Abingdon, OX14 1RG, UK.

Transferrin glycans as such have also been extensively studied: reference is made, of course in a non-limitative manner to general publications describing them, for instance the publication titled "Comparative study of the primary structures of sero-, lacto- and ovotransferrin glycans from different species" of Geneviève Spik et al., in Biochimie 70 (1988) 1459–1469, which describes transferrin glycans obtained from various mammalian species.

As glycoproteins, all transferrin of human and animal origin contain carbohydrates in amounts varying from 2 to 12%. Human serum transferrin has been found to present a microheterogeneity based on the existence of bi- and triantennary glycans of the N-acetyl-lactosaminic type. Three carbohydrate molecular variants of transferrins could be distinguished: Tf-I (less than 1%) containing two triantennary glycans, Tf-II (approx. 17%) with one triantennary and one biantennary glycan and Tf-III (approx. 82%) containing two biantennary glycans. The relative proportions of these variants were found to change in women in the last trimester of pregnancy, the variants I and II showing an increase in contrast to variant III, which was found to decrease to approx. 67% (see Leger et al. referred to hereafter). In addition, it has been established, that human sero-transferrin contains two asparagine glycosylation sites in the C-terminal part of its single polypeptide chain and that the glycans are fully sialytated and not fucosylated. Like the corresponding transferrin, the glycans which can be obtained therefrom display similar microheterogeneities.

Detection of the mammalian species from which particular transferrin glycans originate can be carried out by any person skilled in the art, e.g., by reaction of these glycans with sets of antibodies previously obtained against glycans of a number of different mammalian species, among which presumably that of the species from which the glycans under study may originate. By way of non-limitative illustration, recourse can be had to a method of the type disclosed in the publication titled "Physiological significance of the marked increased branching of the glycans of human serotransferrin during pregnancy" of Didier Léger et al. in Biochem. J., 257: 231–238 (1989) (Printed in Great Britain).

For instance transferrin glycans obtained from a human may be detected by an immunological reaction with antibodies specific to human glycans—or even to the corresponding human transferrins and then with horse-radish-peroxidase—conjugated second antibodies raised against tlg6, in accordance with Trowbridge et al. (1987) Proc. Natl. Acad. Sci. U.S.A. 79: 1175–1179 and Burnette et al. (1981) Anal. Biochem. 112: 195–203.

Of course other types of reactions can be envisaged for the same purpose, e.g., by comparative analysis of the electrophoretic behavior of the glycans under study and standards obtained from transferrins themselves obtained from different mammalian species.

A preferred composition according to the invention comprises the glycans obtained from transferrins also obtained from the donor of the antigens to be transplanted in the recipient host. These glycans can be obtained from said transferrin by any of the well known methods applicable to the removal of the polypeptide moieties and recovery of the corresponding glycans, e.g., a method of hydrazinolysis such as disclosed in the publication of S. Takasaki et al. titled "Hydrazinolysis of Asparagine-Linked Sugar Chains to Produce Free Oligosaccharides in "Methods of Enzymology (1982) Vol.83: 263–268, or in the publication of T. Patel et al., titled "Use of Hydrazine to Release in Intact and Unreduced Form both N- and O-Linked Oligosaccharides from Glycoproteins" in Biochemistry (1993) 32:679–693; or by enzymatic cleavage in the presence of a neuramididase or an endoglycosidase activity, such as that produced by *Flavobacterium meningosepticum*, as disclosed by J. H. Elder et al. (1982) in the publication titled "Endo-β-N-Acetylglucosaminidase F: Endoglycosidase from *Flavobacterium meningosepticum* that cleaves both high-mannose and complex glycoproteins" in Proc. Natl. Acad. Sci. U.S.A., Vol. 79:4540–4544, August 1982, or in the presence of the endo-β-N-acetylglucosaminidase F (Endo F) or peptide: N-glycosidase F (PNGase F) also obtainable from cultures of *Flavobacterium meningosepticum* as disclosed by A. L. Tarentino et al. in the publication titled "Deglycosylation of Asparagine-Linked Glycans by Peptide: N-Glycosidase F".

Reference can also be made to the techniques generally disclosed in "Tools for glycobiology" supra.

However like in the case of transferrin, preferred biologically active compositions include pooled transferrin-derived glycans obtained from a number of donors sufficient to allow said pooled transferrin-derived glycans to contain all the phenotypic information required to ensure for an induction of immune specific tolerance against antigens of a determined allogeneic or xenogeneic donor in an immuno-depressed host grafted with said antigens, after that host had been administered an amount of such pooled transferrin-derived glycans effective to induce said immune specific tolerance.

Pooled transferrin-derived glycans of human origin can be obtained from transferrins which are themselves available in the trade: see "Tools for Glycobiology" already of record. Human transferrin-derived glycans, substantially free of the transferrin polypeptide moieties are available, e.g., at Oxford Glyco Systems, Inc.

BRIEF SUMMARY OF THE INVENTION

Like for the transferrin, the serological detection of a sufficient number of the dominant HLA antigens provides nonetheless an adequate verification system of whether the plasma pools from which the corresponding pooled glycans are to be obtained originated from a sufficient number of donors. For instance a preferred starting plasma pool should also prove to contain at least 4 serologically determinable antigens of each of the so-called HLA-A, HLA-B, HLA-C, HLA-D and HLA-DR series.

It will further be appreciated that, as this will be further discussed hereafter, the results—e.g., those illustrated hereafter—obtainable with transferrin-derived glycans also originating from the donor of the antigens are of great assistance in determining the degree of fitness of pooled transferrin-derived glycans to achieve similar induction of immune tolerance against the antigens transplanted into a recipient host. The closer the results produced in the same experimental protocol by the pooled glycans to the results obtained with glycans derived from the antigen donor himself, the better the "phenotypic matching" of the pooled glycans with the donor's organism.

It will also be readily apparent that the greater the number of instances in which a given composition containing pooled glycans will provide as efficient an induction of immune tolerance in recipients against antigens of different donors as the immune tolerances induced in the same recipients by the corresponding "individual glycans" provided by the same donors respectively, the greater the "universality" of the pooled glycans of said given biological composition. This "universality" should be all the greater as the pooled glycans will also be originating from a greater number of persons. It is then reflected by a similar capability of the pooled transferrin glycans to induce in the recipients, in similar testing protocols, substantially the same effects, or effects of a same order of magnitude, as those achieved in the recipients by the "individual glycans" also obtainable from the respective donors of the antigens whose transplantation into any recipient is to be achieved. The said effects e.g., are those described more fully in the examples which follow, i.e., the inability to "recognize" the donor lymphocytes and to mount an immediate- or a delayed-type immune response against the antigens of that donor, an absence of cytotoxic antibodies in the "tolerant" recipient's serum against the donor's lymphocytes, an inability of "tolerant" recipient to mount a cell-mediated immune reaction in vivo against the donor's leukocytes, an in vitro lack of reactivity of the splenocytes of the "tolerant" recipient towards irradiated donor's lymphocytes, etc.

It must further be appreciated that the expression "transferrin glycans", i.e., glycans essentially free of the transferrin peptide moieties, do also cover but parts of these glycans, e.g., such glycans freed of part or all of one of the antennary glycan chains when it includes several of these chains, or partially desialylated chains, or a single of these antennary glycan chains, in either sialylated, or partially desialylated form, of course provided that the so-modified glycans or glycan parts do not loose their ability to induce the immune-tolerance effects of the non-modified ones, e.g., as assayable by the assay procedures disclosed in the examples.

The invention also concerns the combination of the pooled transferrin-derived glycans and of at least one immunosuppressive drug, e.g., prednisolone, cyclophosphamide, cyclosporin, FK-506 or methotrexate, particularly for use in a human host under the appropriate sequence of administrations, to induce immune tolerance in the host against allogeneic or xenogeneic antigens to be grafted in said host.

DETAILED DESCRIPTION OF THE PREFERRED EMBODIMENTS OF THE INVENTION

As will be seen hereafter the immuno-depression can be achieved by an administration to the host of an immunosuppressive drug, e.g., cyclosporin, prednisolone, cyclosphosphamide, etc. or by irradiation.

It has been found that in animals complete destruction of the immune-system of the recipient host undergoing bone marrow transplantation may not be necessary. The use of chemical immunosuppressants, in conjunction with the pooled transferrin-derived glycans, in the appropriate sequences of administration as discussed hereafter may thus be preferable to lethal irradiation. In leukemic patients already undergoing an immunosuppressive chemotherapy, allogeneic or xenogeneic bone marrow grafting, where hold appropriate, may even no longer require an additional administration of an immunosuppressant, in conjunction with both the administration of the pooled transferrin-derived glycans and the transplantation of bone marrow cells. Partial or total body irradiation as preferably proposed in the grafting protocols proposed by the Applicant in his earlier publications or patents may no longer be required.

After administration of the appropriate pooled transferrin glycans transplantation of bone marrow may be replaced by transplantation of allogeneic or xenogeneic peripheral blood progenitor cells mobilized from the donor's bone marrow into the peripheral blood by administration of cytokines like granulocyte-macrophage colony stimulating factor (GM-CSF) or Multipotential-CSF (Interleukin-3) and harvested by leukapheresis using a cell separator system.

In the case of organ transplantation, donor's antigens to be initially presented to the recipient host in combination with the appropriate transferrin glycans before transplantation of the organ itself may consist of the "buffy coat" or leukocytes from the donor's peripheral blood after centrifugation, containing granulocytes and lymphocytes with HLA-specific antigenic markers of the individual donor. As with bone marrow transplantation, the donor's buffy coat may also be replaced by allo- or xenogeneic peripheral blood progenitor cells, mobilized into the peripheral blood and harvested as described. Most preferably, this presentation of the antigens is done after chemical immunosuppression at the bottom line of suppression of the immune system and before the endogenous reconstitution starts. The stage of immunosuppression can be evaluated by leukocyte counts in the peripheral blood. Apparently best results are obtained when the administration of transferrin glycans and the initial presentation of donor antigens take place just at the beginning of the endogenous reconstitution of the immune system, which follows the chemical immuno-suppression. The early presentation of transferrin glycans (donor-type or pool) together with antigens (e.g., at day 3 in the mouse model of FIG. 1 reported hereafter) will produce tolerance in said human-to-mouse model. Therefore important elements of this invention comprise the administration of transferrin glycans (donor-type or pool) and the timely injection of specific donor antigens, which will induce possibly a selection or deletion of immune reactive cells and thus a specific immune tolerance, both in the allogeneic as well as in the xenogeneic approach.

The same considerations do of course apply to other kinds of antigens. Needless to say that the timing and sequence of administration will have to be studied in each case. The organ to be grafted should not be administered too late after the immunosuppression and the initial presentation of transferrin glycans and antigen, particularly when antigen reactive cells will already have been produced again by the recipient host organism. In such event, the recipient host organism may no longer become tolerant.

The invention is not limited to human pooled transferrin-derived glycans, particularly for the above-mentioned uses. It also extends to pooled transferrin-derived glycans of animal origin, particularly for use in conjunction with the grafting even in man of xenogeneic cells, tissues or organs obtained from the same animal species as the pooled transferrin.

[A] Preparation of Transferrin (Tf)

A pool of human plasma (ca. 1000 donors), iron saturated with $Fe^{3+}$ according to Bates G. W. et al, J. Biol. Chem. 1973, 248:3228–32, is diluted in phosphate buffer and diafiltered on hollow fibers, cut-off 30,000 to remove $Fe^{3+}$ excess, stored one night at 4° C. and filtered through 0.45 μm sterile membranes. The purification procedure consists of two chromatographic steps on ion exchangers, by using buffers at suitable ion strength and pH, in order to selectively remove contaminants such as albumin and immunoglobulins and hence to elute Tf with a purity >95%. After diafiltration to re-establish physiological salt conditions, the solution of apo- or iron-saturated Tf is freeze-dried.

Extraction procedures of transferrins are well known. Some of them are recalled in Applicant's earlier patent EP 0426924 or in the Clinica Chimica Acta publication already referred to hereabove.

Human pooled transferrins may for instance be obtained as disclosed hereinafter.

[B] Preparation of Transferrin-Derived Glycans

Glycans are isolated from human Tf-pool (ca 1000 donors), by the hydrazinolysis method carried out as disclosed in the publication of S. Takasaki et al. referred to above. 1 mg Tf pool contains approximately 20 μg of glycans. In all experiments reported hereafter glycans were used at a dose of 5 μg/mouse i.p., which corresponds to glycans content in the usual dose of Tf (200 μg/mouse) in previous experiments.

[C] Induction of Transplantation Tolerance

The experimental protocols which have been used are briefly recalled hereafter, prior to being set forth subsequently in a more detailed manner.

Prednisolone (Pr) and cyclosphosphamide (Cy) were chosen as immunosuppressants; their respective dosages were adjusted in different mouse strains according to changes in their immunological parameters. By using this model, the first indications of the tolerance-inducing activity of Tf-glycans were observed in preliminary studies on the immune response of mice to human erythrocytes. It was found that human Tf-glycan treatment in immunosuppressed and antigen treated mice inhibits the primary and the secondary immune response to human red blood cells (HRBC) (Tables 2A and 2B).

Since histocompatibility antigens are presented predominantly on leukocytes, it was important to know whether Tf-glycan treatment can induce donor-specific transplantation tolerance in mice injected with peripheral blood "buffy coat" leukocytes. In fact, the abrogation of a cell-mediated immune response towards the Tf-glycan donor tissue antigens was demonstrated with the popliteal lymph node assay in chemically immunosupressed mice treated with Tf-glycan of the donor.

Also absence of donor-specific antibody- and complement-mediated cytotoxicity of mouse serum towards human lymphocytes in chemically immunosuppressed mice treated with human individual Tf-glycans or pooled Tf-glycans was confirmed by trypan-blue exclusion assay (Tables 6A and 6B).

From the data presented here, it is possible to see that also the administration of glycans from a human plasma pool, combined with critically timed presentation of individual specific cell antigens (leucocytes) can produce a state of immunological tolerance. Besides tolerance-inducing properties, human pooled Tf-glycans also possess a remarkable immunoprotective activity by preventing thymus involution and lymphopenia and by increasing the survival rate of chemically immunosuppressed mice.

The above mentioned human-to-mouse model and the results point to a clear-cut tolerance-inducing effect of human glycans by sequential and/or combined administrations of pooled Tf-glycans and cell antigens. Individual Tf-glycans alone are not immunosuppressive per se and are unable to produce tolerance to human antigens in the mouse.

The implication deriving from the disclosed models are obvious. Such transplantation system should be adaptable to larger mammals and to man. In addition, the understanding of the mechanism by which transferrin-derived glycans from plasma pools produce tolerance certainly deserves intensive investigations for a possible adaptation of the model to a number of pathological conditions such as cancer, autoimmune disease, immunodeficiency diseases (e.g., AIDS), genetic defects or diabetes.

In order to fully illustrate the present invention and advantages thereof, the following specific examples are given, it being understood that the same are intended only as illustrative and in nowise limitative.

In the course of the description the following abbreviations were used.

ABBREVIATIONS

Ag=antigen
BM=bone marrow
BMT=bone marrow transplantation
Con A=concanavalin A
Cy=cyclophosphamide
HRBC=human red blood cells
HSA=human serum albumin
IS=immunosuppression
i.p.=intraperitoneally
MTT=(3-[4,5-Dimethylthiazol-2-yl]-2,5-diphenyltetrasolium bromide)
OD=optical density
PLNT=popliteal lymph node test
Pr=prednisolone acetate
Tf=transferrin
Tf glycans=glycans obtained from transferrins Materials and Methods Animals Adult inbred, 3 to 8 month-old, male or female C57BL/6 or BalB/c mice maintained in our animal quarters under conventional conditions were used. The mice received water and fodder ad libitum and the room temperature was 21–22° C.

Immunosuppressive Drugs for Immunosuppression (IS)

Prednisolone acetate (Pr) was purchased from FLUKA Inc., Buchs, Switzerland. It was injected once i.p. as a 1:10 ethanol-water suspension immediately after preparation. Cyclophosphamide (Cy) was purchased from FLUKA and dissolved with water shortly before i.p. injection. Doses and schedule of injection were as indicated in the single experiments.

Preparation and Purification of Transferrin (Tf)

Ferric sulphate and nitrilotriacetic acid (purity 99.5%) used for ferric-nitrilotriacetate preparation was from SIGMA. Sodium bicarbonate was from Merck (Darmstadt, Germany). Salts used for buffers were from Carlo Erba (Milano, Italy, Pharmaceutical type). Diafiltration and concentrations were carried out in a tangential flow system, with ultrafiltration membranes cut-off=30,000. DEAE-Sepharose and CM-Sepharose were from Pharmacia (Uppsala, Sweden). The chromatographic system was based on preparative chromatographic columns connected with a peristaltic pump P1, monitor UV and recorder from Pharmacia. Virus inactivation was performed in a thermostatic-controlled water bath. Total proteins were measured by the method of Lowry et al. against a standard of bovine serum albumin (Pierce, Amsterdam, Netherlands). Antigen protein was determined by radial immunodiffusion with Nor-Partigen Tf and serum protein standard from Behring (Marburg, Germany). Agarose gel electrophoresis was performed with a Helena millipore (Milford, USA) 625 LC chromatograph; the conditions were the followings: column TSK3000SW (75 mm×600 mm); flow rate 0.8 ml/min; mobile phase phosphate 0.05 M, sodium chloride 0.15 M, Na N3 0.05%, pH 7; detector UV Merck-Hitachi L4200 (wavelength 280 nm); integrator-recorder Perkin Elmer LCI-100 (Norwalk, USA). The purification process was as follows: plasma was initially saturated with iron by the addition of sodium bicarbonate and ferric-nutrilotriacetate (FENTA) according to Bates & Schlabach. Plasma was then diluted and diafiltered against phosphate buffer 10 mM prior to loading onto a column with DEAE-Sepharose. The column was eluted with phosphate buffer 50 mM, obtaining a Tf fraction contaminated by immunoglobulins. This fraction was diafiltered against phosphate buffer with a different pH, and loaded onto a column with CM-Sepharose. The flow-through was a Tf fraction with a $\geq 95\%$ purity. The Tf solution was concentrated and virus-inactivated with a pasteurization step at 60° C. for 10 hours, in the presence of suitable stabilizers. After diafiltration to eliminate the stabilizers added for the heating treatment, the Tf concentrate was sterile-filtered, dispensed into vials, freeze-dried and stored at +4° C. Tf obtained with this purification procedure was apo-Tf. To obtain iron-Tf, an additional saturation step with ferric-nitrilotriacetate and diafiltration for eliminating free ferric ions were used. Acceptable endotoxin values in Tf preparations were below 0.7 ng/mg (Limulus assay).

a) Drug-induced Immunosuppression and Evaluation of its Efficacy and Duration

Figure 1:
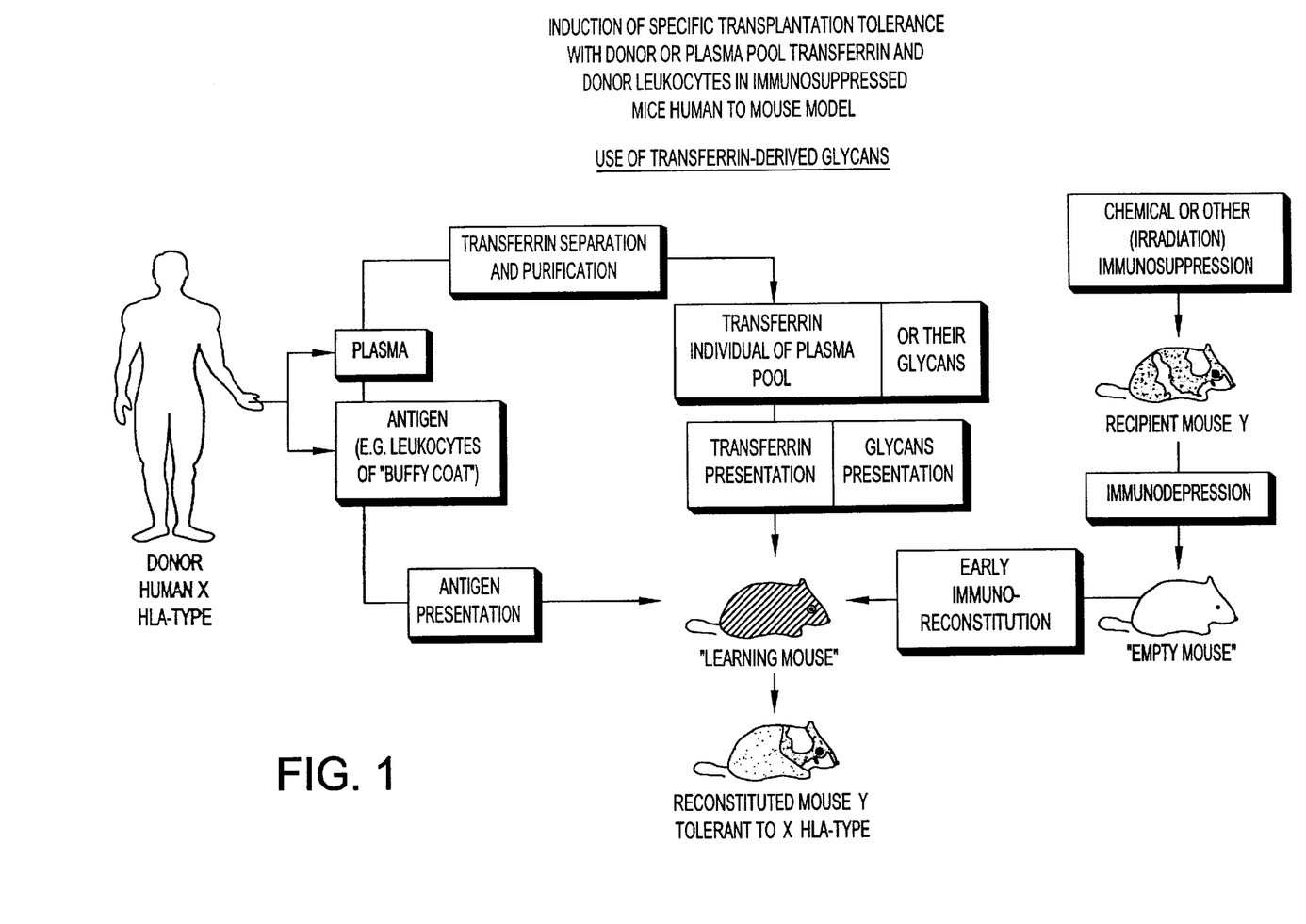
FIG. 1 is an illustration depicting the use of transferrin-derived glycans in conjunction with immunosuppression of the induction of transplant tolerance.

The basic idea underlying our model was that the presentation of Tf or Tf-glycans from a species- or strain-different donor must take place in a condition of complete or very deep depletion of mature immunocytes and before or at the beginning of endogenous reconstitution or repopulation of immune cell producing organs (e.g., the thymus or the bone marrow), combined with presentation of donor- and Tf-matched or Tf-glycan-matched antigens in the course of regeneration and maturation of immunocytes in the BM and in the thymolymphatic tissues (see FIG. 1: the "empty mouse" model). We thought that administration of Tf or Tf-glycans must continue at the time of, and after immunization, until all putative antigen-reactive cells have maturated to a stage leading to specific tolerance or to areactivity-unresponsiveness. For this purpose numerous experiments were initially carried out with mice in order to establish the most suitable type of immunosuppressive treatment and schedule of injection which would induce a durable and profound cytolytic and cytotoxic effect on thymic and BM cell populations and consequently a temporary abrogation of antibody production and cell-mediated immune reactions. Several drugs alone or in combination were studied for their capacity to produce a temporary but deep depression of immunity as e.g., busulphan, azathioprine, cyclosporin, methotrexate, cyclophosphamide, prednisolone. At the end of our long-term trials, a combination of prednisolone acetate (Pr) and cyclophosphamide (Cy) was chosen which produced a profound and durable immunosuppression (IS) for two-three weeks without severe side-effects and elevated mortality. As can be seen in Table 1, the IS with a combination of Pr and Cy resulted in an almost complete BM cell depletion at day 3 and day 4 of the experiment. This depletion was more prolonged when the mice received 200 mg/Kg Cy. In this case the reconstitution started at day 5 (Table 1). It is also visible that IS produced a drastic reduction of peripheral blood leukocytes which were most reduced at day 4 and day 5 of the experiment.

TABLE 1

DEPLETION AND RECOVERY OF NUCLEATED CELL NUMBER IN THE BONE MARROW OR IN PERIPHERAL BLOOD OF MICE AFTER CHEMICAL IMMUNOSUPPRESSION (IS)

| Cell counts after IS[a] | Leukocytes (x $10^6$/ml) | | Lymphocytes (x $10^6$/ml) | | Tibia[b] (x $10^6$) | |
|---|---|---|---|---|---|---|
| | 100 mg/kg Cy | 200 mg/kg Cy | 100 mg/kg Cy | 200 mg/kg Cy | 100 mg/kg Cy | 200 mg/kg Cy |
| day 0[c] | 5.20 ± 0.70 | 5.20 ± 0.70 | 3.60 ± 0.50 | 3.60 ± 0.50 | 7.00 ± 1.40 | 7.00 ± 1.40 |
| day 2 | 2.40 ± 0.40 | 0.60 ± 0.20 | 1.10 ± 0.20 | 0.15 ± 0.06 | 1.20 ± 0.20 | 1.00 ± 0.03 |
| day 3 | 1.70 ± 0.40 | 0.50 ± 0.10 | 0.70 ± 0.14 | 0.14 ± 0.02 | 1.00 ± 0.03 | 0.50 ± 0.03 |
| day 4 | 0.90 ± 0.50 | 0.20 ± 0.10 | 0.30 ± 0.15 | 0.07 ± 0.03 | 1.10 ± 0.10 | 0.50 ± 0.10 |
| day 5 | 0.70 ± 0.50 | 0.02 ± 0.02 | 0.46 ± 0.30 | 0.01 ± 0.00 | 2.00 ± 0.30 | 1.20 ± 0.02 |
| day 6 | 1.60 ± 0.00 | 0.40 ± 0.20 | 1.00 ± 0.35 | 0.20 ± 0.10 | 3.40 ± 0.40 | 1.50 ± 0.10 |
| day 7 | 5.50 ± 0.70 | 1.20 ± 0.60 | 2.80 ± 0.20 | 0.60 ± 0.20 | 5.50 ± 0.90 | 3.40 ± 1.00 |

[a]IS — Pr at the dose of 90 mg/Kg and Cy at the dose of 100 mg/Kg or 200 mg/Kg were injected on day 0. The injection of Cy was repeated at the same dosage on day 1.
[b]The BM cells were suspended in 0.5 ml medium from single tibiae and counted.
[c]-before immunosupression. The values are Means ± SE. For each point three mice were used.

b) Effect of Tf-glycans on Antibody Production to Human Cell Antigens in IS Mice Many experiments and trials in the course of four years preceded the conclusive model illustrated in FIG. 1. In order to develop the presently adopted model for induction of xeno-"tolerance" (human-to-mouse), human Tf-glycans were used.

The following assays, which aim at evaluating the effect of Tf-glycans on the secondary immune response of mice to human red blood cells (also obtained from the donor whose "buffy coat" leukocytes were used for immunization) were performed in chemically immunosuppressed mice.

Balb/c mice were chemically immunosuppressed by injecting 90 mg/kg prednisolne (Pr) and 100 mg/kg cyclophosphamide (Cy) i.p. on day 0. On day 1, 100 mg/kg Cy were injected again i.p. The immunosuppressed mice were daily injected i.p. from day 3 to 9 and from day 16 to 18 with 200 µg Tf pool purified from human blood plasma pool in 0.5 ml (Group 2) or with 5 µg Tf-glycans purified from human Tf pool (Group 3) or received 0.5 ml saline i.p. (Group 4). All the mice including non-IS Group 1 were immunized twice i.p. with human antigens, namely $1.0 \times 10^6$ human peripheral blood "buffy coat" leukocytes in 0.3 ml on day 3 and on day 16. The bleeding was performed on day 31 of the experiment, serum samples were collected and stored at −70° C. until the assay.

The results are reported in Tables 2A and 2B hereafter.

TABLES 2A and 2B

TABLE 2A

INDUCTION OF DONOR-SPECIFIC TOLERANCE WITH GLYCANS EFFECT OF GLYCANS ON THE SECONDARY IMMUNE RESPONSE TO HUMAN RED BLOOD CELLS (HRBC)° IN CHEMICALLY IMMUNOSUPPRESSED MICE.
(Exp. 36, day 31)

| | Groups | $-\log_2$ antibody titers secondary response |
|---|---|---|
| 1. | normal immunized control | 8.0 ± 0.3 n = 5 |
| 2. | IS + Tfpool$_{human}$ | 6.0 ± 1.5 n = 3 |
| 3. | IS + Glycans | 4.0 ± 0.6* n = 4 |
| 4. | IS + saline | 8.3 ± 0.3 n = 3 |

IS—immunosuppresion; Tf—transferrin; n—number of mice per group;
*$p < 0.05$ vs Gr. 1,4

TABLE 2B

INDUCTION OF DONOR-SPECIFIC TOLERANCE WITH GLYCANS EFFECT OF GLYCANS ON THE SECONDARY IMMUNE RESPONSE TO HUMAN RED BLOOD CELLS (HRBC)° IN CHEMICALLY IMMUNOSUPPRESSED MICE.
(Exp. 37, day 30)

| | Groups | $-\log_2$ antibody titers secondary response |
|---|---|---|
| 1. | normal immunized control | 8.0 ± 0 n = 4 |
| 2. | IS + Tfpool$_{human}$ | 5.8 ± 0.6 n = 5 |
| 3. | IS + Glycans | 3.8 ± 0.6* n = 5 |
| 4. | IS + saline | 6.4 ± 0.5 n = 8 |

IS—immunosuppresion; Tf—transferrin; n—number of mice per group;
*$p < 0.01$ vs Gr. 1,4

The results obtained indicated that injection of Tf-glycans from human plasma pool into IS mice resulted in a considerable lasting unresponsiveness or marked decrease of production in most of the mice of antibodies against randomly chosen donors of human peripheral blood cell antigens. It can be seen (Tables 2A and 2B) that injection of viable human peripheral blood cells into the IS and human Tf-glycans treated mice resulted in lasting inhibition of the immune response to human antigens. No abrogation or lasting diminution of the antibody response could be seen when the IS and human-antigen-immunized mice had been injected with saline in the course of the immune restoration after IS.

In summary, these preliminary findings served only to establish that presentation of both human Tf or human transferrin-glycans from plasma pool and individual-specific human cell antigens in the IS murine host resulted in a durable inability of most of the mice to mount a normal immune response to human antigens;

c) Human Tf-glycans Alone do not Exert an Immunosuppressive Effect in Mice

Repeated injections of human glycans into mice did not impair or decrease their primary or secondary (memory) response to human erythrocytes and no effect could be observed on peripheral blood leukocyte count and on the delayed type hypersensitivity response (Oxazolone test). Human Tf glycans do not exert themselves an immunosuppressive activity in mice (data not reported here).

The absence of direct immunosuppressive effects induced by Tf-glycans as well as their inability of affecting both the antibody response and the cell-mediated immunity in normal mice are reflected by the results presented in Tables 3 and 4 hereafter, as a result of assays which were carried out as follows.

10% human erythrocytes in 0.2 ml i.p. on day 3 and on day 9.

Balb/c mice (3 animals/group) were daily injected intraperitoneally (i.p.) for 10 days with 5 μg of glycans in 0.5 ml (Group 1). Group 2 was similarly injected with saline while Group 3 was left untreated. On day 3 and again on day 9, all mice were immunized with 10% human erythrocyte suspension in 0.2 ml.

The bleeding was performed on day 9 and on day 14 of the experiment. The primary and the secondary immune response were measured by using the direct hemagglutination assay.

As apparent from the results displayed in Table 4, glycans from transferrin have no immunosuppressive effects and do not affect the antibody response in mice.

The effect of glycans on the primary and the secondary immune response (IR) to human red blood cells (HRBC) in normal mice was tested upon using the following protocole.

HRBC—10% human erythrocytes in 0.2 ml i.p. on day 3 and on day 9. Balb/c mice (3 animals/group) were daily injected intraperitoneally (i.p.) for 10 days with 5 μg of glycans in 0.5 ml (Group 1). Group 2 was similarly injected with saline while Group 3 was left untreated. On day 3 and again on day 9, all mice were immunized with 10% human erythrocyte suspension in 0.2 ml.

TABLE 3

Effects of glycans or the primary and secondary immune response (IR) to human red blood cells (HRBC) in normal mice.

| Groups | N mouse serum | $-\log_2$ Ab titers primary IR | secondary IR |
|---|---|---|---|
| Gr. 1 | 1. | 6.0 | 6.0 |
| HRBC + glycans | 2. | 6.0 | 8.5 |
| n = 3 | 3. | 6.0 | 8.0 |
| Mean ± SE | | 6.0 ± 0 | 7.5 ± 0.8 |
| Gr. 2 | 1. | 6.0 | 8.0 |
| HRBC + saline | 2. | 4.0 | 7.0 |
| n = 3 | 3. | 6.0 | 9.0 |
| Mean ± SE | | 5.3 ± 0.6 | 8.0 ± 0.6 |
| Gr. 3 | 1. | 6.0 | 8.0 |
| HRBC | 2. | 5.0 | 7.0 |
| n = 3 | 3. | 6.0 | 7.0 |
| Mean ± SE | | 5.7 ± 0.3 | 7.3 ± 0.4 |

Similar results appear in Table 4, which show that glycans obtained from single transferrin batches and glycans from human transferrin pool neither have immunosuppressive effects nor affect cell-mediated immunity in normal mice.

TABLE 4

Effect of Glycans on the primary and secondary delayed-type hypersensitivity (DTH) response in normal mice

| Group | No of mice | Ear thickness (× 0.01 mm) | | | | | |
|---|---|---|---|---|---|---|---|
| | | before Ch-1 | after Ch-1 | $\Delta_I$ | before Ch-2 | after Ch-2 | $\Delta_{II}$ |
| Gr. 1 | 1. | 25.0 | 27.5 | 2.5 | 24.5 | 28.5 | 4.0 |
| Glycans | 2. | 24.5 | 27.5 | 3.0 | 24.0 | 26.0 | 2.0 |
| | 3. | 25.5 | 28.5 | 3.0 | 25.5 | 29.0 | 3.5 |
| Mean ± SE | | | | 2.8 ± 0.2 | | | 3.2 ± 0.6 |
| Gr. 2 | 1. | 24.5 | 27.5 | 3.0 | 25.5 | 27.5 | 2.0 |
| saline | 2. | 25.5 | 28.5 | 3.0 | 26.0 | 28.5 | 2.5 |
| | 3. | 25.0 | 29.0 | 4.0 | 26.5 | 28.5 | 2.0 |
| Mean ± SE | | | | 3.3 ± 0.3 | | | 2.2 ± 0.2 |
| Gr. 3 | 1. | 24.5 | 28.0 | 3.5 | 25.0 | 29.0 | 4.0 |
| untreated | 2. | 25.5 | 28.5 | 3.0 | 26.0 | 28.0 | 2.0 |
| | 3. | 24.5 | 27.5 | 3.0 | 25.0 | 28.0 | 3.0 |
| Mean ± SE | | | | 3.2 ± 0.2 | | | 3.0 ± 0.6 |

Ch-1 — Challenge 1 (on day 7); Ch-2 — Challenge 2 (on day 14)

Additional assays, i.e., the mixed lymphocytes culture (MTT assay) and the Trypan blue exclusion assay for measurement of complement-mediated cytolysis, as well as the results obtained are reported hereafter. The general procedures are reported first.

Mixed Lymphocyte Culture (MTT Assay)

a) Culture Medium

Spleen cells from the experimental mice were cultured in a medium with the following composition: 50% RPMI 1640 (SIGMA); 30% Dulbecco's modification of Eagle's medium (DMEM, Seromed, Berlin, Germany); 10% Iscove's modification of Dulbecco's medium (IMDM, Seromed); 10% fetal calf serum (FCS, Seromed); 2 mM glutamine, 100 units/ml Penicillin, 100 µg/ml Streptomycin (SIGMA); 29 µM 2-mercaptoethanol (FLUKA).

b) Isolation of Mouse Spenocytes

The mice were sacrificed by cervical disclocation, the spleens removed in aseptical conditions and immersed into RPMI 1640 medium. Each spleen from the experimental mice was teased separately in a Potter glass with Teflon pestle and the splenocyte suspensions from individual mice were prepared in the culture medium. Erythrocytes were eliminated by osmotic shock: the spienocyte suspension was added to the same volume of bidistilled water. After 5 min the mixture was diluted with the culture medium containing double NaCI concentration. After centrifugation (1500 rpm, 10 min, room temperature) the supernatant was removed and the cells were resuspended with the culture medium to the final concentration of $2 \times 10^6$ cells/ml. This suspension was distributed into 96-well plates with flat bottom (Falcon, Oxnard, USA) at 100 µl ($2 \times 10^5$ cells) per well.

c) Isolation of Human Lymphocytes Target, Target Cell Irradition Cell Irradiation and Preparation of Samples Human lymphocytes from heparinized blood of individual donors were isolated by density gradient centrifugation (2000 rpm for 20 min at room temperature) by using Accuspin System Histopaque 1077 (SIGMA). After centrifugation the supernatant was removed and the cells were washed three times with the culture medium and resuspended in this medium to the final concentration of $2 \times 10^6$ cells/ml. The human lymphocytes as well as a part of the mouse splenocytes were irradiated with a total dose of 2500 Rad by using a Gammacell 3000 Elan installation (Nordion Intern. Inc., Canada). The irradiated cells were added to the mouse splenocytes in a 100 µl volume ($2 \times 10^5$ cells) per well. The final culture well contained $2 \times 10^5$ mouse splenocytes and $2 \times 10^5$ irridiated cells (human lymphocytes or mouse splenocytes) in a 200 µl volume.

The following cell combinations were used for the mixed lymphocytes culture: A—splenocytes from experimental mice (responding cells); A*—irradiated mouse splenocytes from intact mice of the same strain, sex and age; B*—irradiated human lymphocytes (stimulating cells). The following combinations were included: 1. A+B* (stimulation of mouse splenocytes by human antigens); 2. A+A* (background or non-specific activity); 3. A+ConA (ability of mouse spienocytes to respond). In the last case 10 µl (10µl/ml) ConA (SIGMA) were added to each well containing A cells, so that the final volume of this combination was 110 µl per well. A+B and A+A* combinations were evaluated in 4–5 parallel wells for each individual cell mixture suspension A+ConA combination was evaluated in two parallel wells for each splenocyte suspension.

The cell combinations were maintained in a humidified atmosphere of 5% $CO_2$—95% air at 37° C. for 5 days. On day 2 of culture, 100 µl of medium were eliminated from all wells except the (A+ConA) combination, and 100 µl of fresh culture medium were added to all wells.

The MTT Assay

The assay is dependent on the cellular reduction of MTT by the mitochondrial dehydrogenase of viable cells to a blue formazan product which can be measured spectrophotometrically.

The MTT assay was performed according to Mossman with some modifications. MTT (3-[4,5-Dimethylthiazol-2-yl]-2,5-diphenyltetrasolium bromide) (SIGMA) was dissolved in phenol red-free RPMI 1640 (SIGMA) at a final concentration of 0.5 mg/ml (MTT stock solution) filtered through a 0.22 µm filter and used on the same day. After 5 days of culture the medium was removed from the plates by aspiration and 100 µl aliquot of MTT stock solution was added to each well of the assay plates which were then incubated for further 4 hours at 37° C. in the $CO_2$ incubator. Then the supernatant from the wells was removed by aspiration. Acid-isopropanol (100 µl of 0.04 N Hcl in isopropanol) was added to all wells and mixed thoroughly to dissolve the dark blue crystals. Ten to fifteen min later the plates were read with a Microelisa Reader (SRAT automatic, 90139, Austria) using a test wavelength of 570 nm and reference wavelength of 690 nm.

Optical density (OD) of the A+B* combination corresponds to intensity of two components: background activity of mouse splenocytes and their proliferative reaction to human antigens, while OD of the A+A* combination measures the background activity of mouse splenocytes under study. The difference between $OD_{A+B}$ and $OD_{A+A^*}$ was considered as the true reaction of mouse splenocytes to human antigens. To combine the results of similar experiments, the magnitude of this reaction was expressed as percent. The mean value of the reaction in non-immunosuppressed and immunized mice was established at 100%.

Trypan Blue Exclusion Assay for Measurement of Complement-mediated Cytolysis

Lymphocytes were isolated from heparinized blood of human donor by the use of Accuspin System Histopaque 1077 (SIGMA, St. Louis, USA). The cells were washed tree times with isotonic saline and resuspended in concentration 4–6×106 cells/ml. Samples of mouse serum (heat inactivated at 56° C. for 30 min) were dispensed in 25 µl volume. An equal volume of the human lymphocyte suspension was added to each tube and the mixture was incubated at 37° C. for 30 min. Then 50 µl rabbit complement (Rabbit HLA-ABC, SIGMA) was added to each sample, and incubation was carried out for 10 min at 37° C. Controls were set up using normal mouse serum or saline to ensure that the complement is non-toxic. After centrifugation (2000 rpm for 5 min) the supernatant fluid was removed from each tube leaving the cell pellet at the bottom and tubes were immersed into ice. Before reading, 25 µl Trypan Blue solution (SIGMA) was added to each tube and the proportion of stained (non-viable) cells was counted.

Mixed Lymphocyte Culture (MTT Assay)

The data reported in connection with this assay demonstrate that the combined administration of human Tf-glycan-pool and, as antigen, individual human leukocytes in the IS mice induce a profound or complete areactivity of the effector mouse spleen lymphocytes towards the target lymphocytes from the human donor. In fact the activation values in vitro are comparable to those of normal, non-IS and non-immunized mice.

The conditions under which the assays were carried out (legend which follows) and the results obtained appear in Table 5A.

Legend to Table 5A Mixed Lymohocytes Culture (MTT assay) on Day 65 of the Experiment Balb/c mice were chemically immunosuppressed by injecting 90 mg/kg prednisolone (Pr) and 100 mg/kg cyclosphosphamide (Cy) i.p. on day 0. On day 1, 100 mg/Kg Gy were injected again i.p. The immunosuppressed mice were daily injected i.p. from day 3 to day 9 and from day 16 to day 18 with 200 µg Tf pool purified from human Tf pool in 0.5 ml (Group 1) or with 5 µg glycans purified from human Tf pool (Group 2) or received 0.5 ml saline i.p. (Group 3). All the mice including non-IS Group 4 were immunized twice i.p. with human antigens, namely 1.0×106 human peripheral blood "buffy coat" leukocytes in 0.3 ml on day 3 and on day 16. The mice were killed on day 65 of the experiment and mixed lymphocyte culture reaction of mouse splenocytes against human lymphocytes (from the same donor whose "buffy coat" leukocytes were used for immunization) was performed and evaluated by using MTT assay (see Mixed lymphocytes culture, MTT assay).

TABLE 5A

INDUCTION OF TRANSPLANTATION TOLERANCE WITH
Tf POOL AND GLYCANS
MIXED LYMPHOCYTE CULTURE REACTION (MTT-TEST)
DAY 65 OF THE EXP. 37

| Groups | $OD_{A+B^*}$ I | $OD_{A+A^*}$ II | Δ (I − II) |
|---|---|---|---|
| 1. IS + AgV.L. + Tf pool (n = 3) | 0.213 ± 0.040 | 0.165 ± 0.026 | 0.048 ± 0.021° |
| 2. IS + AgV.L. + glycans (n = 3) | 0.214 ± 0.017 | 0.142 ± 0.009 | 0.073 ± 0.009° |
| 3. IS + AgV.L. + saline (n = 3) | 0.244 ± 0.036 | 0.153 ± 0.040 | 0.092 ± 0.010 |
| 4. non-IS + AgV.L. (n = 5) | 0.243 ± 0.063 | 0.110 ± 0.047 | 0.133 ± 0.044 |
| intact (n = 1) | 0.140 | 0.082 | 0.058 |

A — splenocytes from individual experimental mice ($2 \times 10^5$ cells/well), five wells for each mouse in parallel.
B* — irradiated (2500 rad) lymphocytes of V.L. ($2 \times 10^5$ cells/well)
A* — irradiated (2500 rad) syngeneic splenocytes from intact Balb/C mice ($2 \times 10^5$ cells/well)
OD — optical density with a 570 nm test wavelength and a 690 nm reference wavelength.
Δ — the difference between $OD_{experimental}$ and $OD_{base\ line}$
Cell mixture was cultivated during 5 days in $CO_2$ (5%) incubator
°$p_U < 0.05$ vs Gr. 3 (non-parametric statictics U-criterium Wilcoxon-Mann-Whitney)

Results of a same nature were obtained on day 103 of the experiment. The conditions under which the assay was carried out are reiterated hereafter Mixed Lymphocyte Culture (MTT Assay) on Day 103 of the Experiment Balb/c mice were chemically immunosuppressed by injecting 90 mg/kg prednisolone (Pr) and 100 mg/kg cyclophosphamide (Cy) i.p. on day 0. On day 1, 100 mg/kg Cy were injected again i.p. The immunosuppressed mice were daily injected i.p. from day 3 to 9 and from day 16 to 18 with 200 pg Tf pool purified from human blood plasma pool in 0.5 ml (Group 1) or with 5 μg glycans purified from human Tf pool (Group 2) or with 200 μg HSA (Group 3) or received 0.5 ml saline i.p. (Group 4). All the mice including non-IS Group 5 were immunized twice i.p. with human antigens, namely 1.0×10[6] human peripheral blood "buffy coat" leukocytes in 0.3 ml on day 3 and on day 16. The mice were killed on day 103 of the experiment and the mixed lymphocyte culture reaction of mouse splenocytes against human lymphocytes[1] was performed and evaluated by using the MTT assay.

[1]lymphocytes were from the same donor whose "buffy coat" leukocyes were used for immunization.

The results appear in Table 5B hereafter.

Complement Dependent Cytotoxicity of Mouse Serum (Trypan Blue Exclusion Assay on Day 31 and on Day 61 of the Experiment)

Balb/c mice were chemically immunosuppressed by injecting 90 mg/kg prednisolone (Pr) and 100 mg/kg cyclophosphamide (Cy) i.p. on day 0. On day 1, 100 mg/kg Cy were injected again i.p. The immunosuppressed mice were daily injected i.p. from day 3 to 9 and from day 16 to 18 with 200 μg Tf pool purified from human blood plasma pool in

TABLE 5B

INDUCTION OF TRANSPLANTATION TOLERANCE WITH GLYCANS MIXED LYMPHOCYTE CULTURE REACTION (MTT-TEST) DAY 103 OF THE EXP. 36

| Groups | $OD_{A+B^*}$ I | $OD_{A+A^*}$ II | $\Delta$ (I − II) |
|---|---|---|---|
| 1. IS + AgW.P. + Tf pool (n = 4) | 0.157 ± 0.010 | 0.130 ± 0.020 | 0.027 ± 0.012* |
| 2. IS + AgW.P. + glycans (n = 3) | 0.115 ± 0.005 | 0.093 ± 0.017 | 0.022 ± 0.013* |
| 3. IS + AgW.P. + HSA (n = 2) | 0.140 ± 0.031 | 0.062 ± 0.021 | 0.078 ± 0.010 |
| 4. IS + AgW.P. + saline (n = 2) | 0.172 ± 0.027 | 0.122 ± 0.058 | 0.050 ± 0.030 |
| 5. non-IS + AgW.P. (n = 4) | 0.175 ± 0.016 | 0.085 ± 0.015 | 0.089 ± 0.012 |
| intact (n = 1) | 0.056 | 0.012 | 0.044 |

A — splenocytes from individual experimental mice (2 × 10[5] cells/well), five wells for each mouse in parallel.
B* — irradiated (2500 rad) lymphocytes of W.P. (2 × 10[5] cells/well)
A* — irradiated (2500 rad) syngeneic splenocytes from intact Balb/C mice (2 × 10[5] cells/well)
OD — optical density with a 570 nm test wavelength and a 690 nm reference wavelength.
$\Delta$ — the difference between $OD_{experimental}$ and $OD_{base\ line}$
Cell mixture was cultivated during 5 days in $CO_2$ (5%) incubator
*$p < 0.05$ vs Gr. 3; $p < 0.02$ vs Gr 5

Trypan-blue Exclusion Assay

The assay permits testing the permeability of cells after their incubation with antibodies and complement. If cytotoxic antibodies bind to the membranes of target cells, complement is fixed and cell permeability increases. It is used to assess cell permeability or "death" by adding a solution of trypan blue which penetrates into dead cells, but leaves viable cells unstained.

The assays were carried out upon using antigens of different persons (WP and VL).

The assay was made according to the following protocol:

0.5 ml (Group 1) or with 5 μg Glycans purified from human Tf pool (Group 2) or received 0.5 ml saline i.p. (Group 3). All the mice including non-IS Group 4 were immunized twice i.p. with human antigens (Ag. WP and Ag. VL) namely 1.0×10[6] human peripheral blood "buffy coat" leukocytes in 0.3 ml on day 3 and on day 16. The bleeding was performed on day 31 and on day 61 of the experiment, serum samples were collected and stored at −70° C. until the assay.

Two series of experiments were ran, the results of which appear in Tables 6A and 6B hereafter.

TABLE 6A

SPECIFIC ABROGATION OF THE IMMUNE RESPONSE WITH GLYCANS COMPLEMENT DEPENDENT CYTOTOXICITY OF MOUSE SERUM EXP. 36 TRYPAN BLUE EXCLUSION ASSAY

| | day 31 | | day 61 | |
|---|---|---|---|---|
| | Lymph. W.P. | Lymph. M.L. | Lymph. W.P. | Lymph. M.L. |
| Groups | % of dead cells | | | |
| 1. IS + AgW.P. + Tf pool | 11.6 ± 4.7° n = 7 | 7.2 ± 4.6* n = 4 | ND | 7.8 ± 2.1° n = 6 |
| 2. IS + AgW.P. + glycans | 7.6 ± 0.8° n = 9 | 4.8 ± 0.9*° n = 10 | ND | 6.7 ± 1.4° n = 8 |
| 3. IS + AgW.P. + saline | 43.4 ± 18.8 n = 5 | 41.6 ± 14.4 n = 7 | ND | 27.4 ± 14.0 n = 5 |

TABLE 6A-continued

SPECIFIC ABROGATION OF THE IMMUNE RESPONSE WITH GLYCANS
COMPLEMENT DEPENDENT CYTOTOXICITY OF MOUSE SERUM
EXP. 36 TRYPAN BLUE EXCLUSION ASSAY

| | day 31 | | day 61 | |
|---|---|---|---|---|
| | Lymph. W.P. | Lymph. M.L. | Lymph. W.P. | Lymph. M.L. |
| Groups | % of dead cells | | | |
| 4. non-IS + AgW.P. | 99.0 ± 0.3 n = 10 | 97.6 ± 1.0 n = 10 | ND | 86.7 ± 6.2 n = 8 |
| compl. control | 5.4 ± 1.2 n = 6 | | 6.2 ± 2.0 n = 2 | |

ND — not determined
*p < 0.05 vs Gr. 3
°$p_U$ < 0.05 vs Gr. 3
$p_U$ — non-parametrical statistics U-criterium (Wilcoxon-Mann-Whitney) for unpaired data.

TABLE 6B

SPECIFIC SUPPRESSION OF THE IMMUNE RESPONSE WITH GLYCANS
COMPLEMENT DEPENDENT CYTOTOXICITY OF MOUSE SERUM
EXP. 37 TRYPAN BLUE EXCLUSION ASSAY

| | day 30 | | day 60 | |
|---|---|---|---|---|
| | Lymph. V.L. | Lymph. A.B. | Lymph. V.L. | Lymph. A.B. |
| Groups | % of dead cells | | | |
| 1. IS + AgV.L. + Tf pool | 63.7 ± 11.9 n = 3 | 22 ± 3.7 n = 3 | 45.3 ± 12.3 n = 3 | 17.5 ± 6.7 n = 3 |
| 2. IS + AgV.L. + glycans | 14.4 ± 2.2* n = 5 | 10.8 ± 5.1* n = 5 | 27.0 ± 7.1** n = 4 | 9.7 ± 1.1° n = 4 |
| 3. IS + AgV.L. + saline | 63.0 ± 12.9 n = 8 | 65.4 ± 12.5 n = 8 | 63.9 ± 11.2 n = 9 | 42.3 ± 18.3 n = 4 |
| 4. non-IS + AgV.L. | 100 ± 0 n = 5 | 97.9 ± 0.7 n = 5 | 99.8 ± 0.2 n = 5 | ND |
| compl. control | 3.8 ± 1.3 n = 5 | | 3.8 n = 1 | |

ND — not determined;
*p < 0.01 vs Gr. 3;
**p < 0.02 vs Gr. 3;
°$p_U$ < 0.05 vs Gr. 3
$p_U$ — non-parametrical statistics U-criterium (Wilcoxon-Mann-Whitney) for unpaired data The compositions of the invention are suitable for use in many areas, some of which have already been referred to earlier. These compositions are suitable particularly for the treatment of patients with the following classes of diseases, all of which would benefit from allogeneic or xenogeneic bone marrow transplantation:

Aplastic anemia; agranulocytosis;
Thalassemia;
Immunodeficiency diseases (AIDS, agammaglobulinemia, etc.);
Leukemias (Myeloblastic, lymphoblastic, erythroblastic, etc.)
Myelomas
Metastizing solid tumors, carcinomas, adenocarcinomas;
Genetic diseases;
Organ transplantation.

Another large group of patients can make use of the invention, e.g., patients undergoing transplantation of organs from man or animals (pig, monkey, etc.) (Acceptance of liver, heart, kidneys, Langerhans islets without rejection reaction).

Whenever required the patient may be preconditioned to the immune acceptance of an organ or tissue from another host, by prior Tf-glycans administration and transplantation of bone marrow or bone marrow stem cells from the host which is also to provide said organ or tissue.

See also general indications supplied by Gluckman E. in its article titled "Bilan actuel de la greffe de moelle osseuse allogénique" (General overview on the graft of allogeneic bone marrow) published in Path. Biol. 1980, 28, N° 1, 5–7. These indications are also applicable here.

The invention finds use e.g., in allogeneic (histoincompatible non-HLA-matched) BMT. whereby the difficulties linked to the finding of a donor should be circumvented to a great extent. The invention is not limited to compositions for use in the graft of allogeneic and xenogeneic BMT only. Their use is to be contemplated in any system aiming at facilitating the engraftment of any type of cells, tissues or organs in any type of mammal including man.

Though the way of administering the composition of the invention and its coupling with the steps involving depression or suppression of the endogeneous immune system in the host to be transplanted with allogeneic on xenogeneic cells should rest with the clinicians, it nevertheless remains that the abovesaid depression or suppression should normally be caused to take place prior to Tf-glycans administration and transplantation.

Noteworthy is the fact that chemical immunosuppression of the receiving host prior to bone marrow transplantation or transplantation of other cells tissues or organs should generally be enough. Full previous destruction of the receiving host's own immune system does not appear as necessary. But the systems used to induce immunosuppression in the host may also combine chemical immunosuppression with more or less limited irradiation, for instance of lymphoid organs only, in order to prevent large irradiation damage (lungs, intestine, etc.). Any cytostatic drug or immunosuppressive drug, e.g., cyclosporin, prednisolone, FK-506 may be given alone or in combination with irradiation to condition the recipient to the transfer of foreign cells or tissues.

Neither are the uses of the compositions of the invention limited to the transplantation of bone marrow only. They become applicable whenever a transfer into the pre-treated host of a new immunological system is required, e.g., for inducing rejection by the host of leukemic cells or solid tumors. Another important use of the invention is in xenogeneic (inter-species), transplantation for example when the donor of bone marrow or organs (e.g., liver, heart, kidney) is the pig or a primate (monkeys) and the recipient is man.

Alternatives in the time points at which the Tf-glycan pools are to be administered to the recipient are contemplated too. They may also be administered to the donor, prior to the transfer of his cells to the recipient. Repeated subsequent administrations of said glycan pools is likely to favor the engraftment-capacity of the bone marrow or others organs or tissue in the recipient, in order to reinforce the tolerance induced towards the grafted bone marrow and organs or tissue of allogeneic or xenogeneic origin.

Pooled Tf-glycans may also be added to bone marrow cultures, to pre-incubate in vitro the donor bone marrow for variable periods (hours or days) before its inoculation in the recipient. This procedure may change and/or improve the engraftment capacity of the donor bone marrow and enhance induction of GvHD-free chimerism.

The compositions of the invention may be administered by any route normally used to enhance the host non-responsiveness to the foreign (allogeneic or xenogeneic) bone marrow and/or organs. Though oral or rectal routes may be contemplated, the preferred ones remain the parenteral routes (intravenous or intramuscular injections).

Though this should not be construed in any limitative manner whatsoever, daily doses of pooled Tf-glycans to the host, after the engraftment of bone marrow and/or organs sought to be grafted has been achieved, should for instance range from about 20 micrograms to 500 micrograms, e.g., from about 50 micrograms to about 200 micrograms per kg body weight of the host. Treatments of that type could last from 10 to 30 days after said engraftment.

However, the treatment with the pooled Tf-glycans may also be pursued days, weeks or months after transplantation, alone or in combination with immunosuppresive drugs such as e.g., cyclophosphamide, cyclosporin, FK-506, methotrexate in all those cases in which the transplanted individual shows signs or symptoms of an ill-functioning hemopoietic system (anemia, leucopenia, thrombocytopenia) or of graft versus host disease and/or immunological deficiencies.

What is claimed is:

1. A method for controlling an immune response to an allograft or a xenograft of foreign tissues or cells in a mammal in need of such treatment, said method comprising the steps of:

(a) immunosuppressing said mammal;

(b) administering pooled transferrin-derived glycans from a mammalian species to said mammal, wherein said transferrin-derived glycans are substantially free of transferrin polypeptide moieties; and (c) grafting said foreign cells or tissues into said mammal, wherein said foreign cells or tissues are from the same mammalian species as said pooled transferrin-derived glycans, thereby controlling said immune response by enchancing host non-responstiveness to said allograft or xenograft.

2. The method according to claim 1, wherein said pooled transferrin-derived glycans are pooled human transferrin-derived glycans.

3. The method according to claim 1, wherein said pooled transferrin-derived glycans contain at least four serologically determinable antigens of HLA-A, HLA-B, HLA-C, HLA-D and HLA-DR.

4. The method according to claim 1, wherein said mammal is immunosuppressed with an immunosuppressive drug selected from the group of prednisolone, cyclophosphamide, cyclosporin, methotrexate and FK-505.

5. The method according to claim 1, wherein said foreign cells are bone marrow cells.

6. The method according to claim 1, wherein said foreign cells are leukocyte cells.

7. The method according to claim 1, wherein said foreign cells are peripheral blood progenitor cells.

8. A method for controlling an immune response to an allograft or a xenograft of foreign tissues or cells in a mammal in need of such treatment, said method comprising the steps of:

(a) immunosuppressing said mammal;

(b) administering transferrin-derived glycans to said mammal, wherein said trannsferrrin-derived glycans are substantially free of transferrin polypeptlide moleties; and (c) grafting said foreign cells or tissues into said mammal, wherein said foreign cells or tissues originate from the same mammalian donor from which said transferrin-derived glycans are obtained, thereby controlling said immune response by enhancing host non-responstiveness to said allograft or xenograft.

* * * * *